United States Patent [19]

Opie et al.

[11] Patent Number: 5,013,305
[45] Date of Patent: May 7, 1991

[54] NEEDLE SAFETY SYSTEM AND METHOD

[76] Inventors: Eric A. Opie, 24186 Alaska Rd., Brier, Wash. 98036; Fred E. Silverstein, 1246 15th Ave. E., Seattle, Wash. 98112

[21] Appl. No.: 212,887

[22] Filed: Jun. 29, 1988

[51] Int. Cl.⁵ ............................................. A61M 5/32
[52] U.S. Cl. .................................. 604/192; 604/198; 604/263
[58] Field of Search ............... 604/198, 192, 263, 110

[56] References Cited

U.S. PATENT DOCUMENTS

| 2,876,770 | 3/1959 | White | 604/198 |
|---|---|---|---|
| 3,134,380 | 5/1964 | Armao | 604/198 |
| 4,329,989 | 5/1982 | Dallons et al. | 604/192 |
| 4,596,562 | 6/1986 | Vernon | 604/192 |
| 4,725,267 | 2/1988 | Vaillancourt | 604/198 |
| 4,735,618 | 4/1988 | Hagen | 604/110 |
| 4,755,170 | 7/1988 | Golden | 604/52 |
| 4,790,828 | 12/1988 | Dombrowshi et al. | 604/198 |
| 4,795,432 | 1/1989 | Karczmer | 604/110 |
| 4,795,443 | 1/1989 | Permenter et al. | 604/198 |
| 4,804,371 | 2/1989 | Vaillancourt | 604/198 |
| 4,822,521 | 4/1989 | Laico et al. | 604/192 |
| 4,846,809 | 7/1989 | Sims | 604/198 |
| 4,850,994 | 7/1989 | Zerbst et al. | 604/198 |
| 4,887,998 | 12/1989 | Martin et al. | 604/110 |
| 4,915,697 | 4/1990 | Dupont | 604/192 |
| 4,955,866 | 9/1990 | Corey | 604/198 |

FOREIGN PATENT DOCUMENTS

WO87/02254 4/1987 Fed. Rep. of Germany .

OTHER PUBLICATIONS

Advertising Notebook of ICU Medical, Inc., all Pages, Compiled by ICU Medical, Inc.

Primary Examiner—C. Fred Rosenbaum
Assistant Examiner—Mark O. Pollutta
Attorney, Agent, or Firm—Seed and Berry

[57] ABSTRACT

A device and method for preventing accidental needle sticks. A sleeve having an annular shaft is slidably connected to a needle. A cord is rigidly affixed to the hub of the needle at one end thereof and to a blocking member at the other end thereof is also slidably coupled to the sleeve. After the needle has been used and is being removed from the patient's body, the sleeve is slid along the needle shaft to cover the tip and pulls the blocking member into position over the sharp tip of the needle. This positively covers the sharp tip of a needle with a puncture-proof blocking member to prevent accidental needle sticks. In alternative embodiments, a resilient member is pressed to align a hole through which the needle is projecting with a hole in a puncture-proof member which is covering the sharp tip of the needle to permit the needle protective device to be slid down the shaft of the needle and the needle to be used. A recessed needle assembly to be used in tandem with a needle assembly, is also disclosed. The recessed needle has a protective wall to prevent accidental needle sticks. An over-cover for the entire needle assembly which may be removed once, but when placed on the hub of the needle after having been used, may not be removed a second time from the needle assembly to provide additional protection, is also disclosed.

The devices disclosed herein can be used for removing fluid from a patient, transferring fluid to or from and IV system, medicine bottles, vacuum test tubes, etc. A complete system having numerous safety features is described that significantly reduces the risk of accidental needle sticks of all types during each stage that a needle is handled.

17 Claims, 8 Drawing Sheets

NEEDLE SAFETY SYSTEM AND METHOD

TECHNICAL FIELD

This invention relates to health care devices, and more particularly, relates to an apparatus and method for preventing accidental needle sticks.

BACKGROUND OF THE INVENTION

Hypodermic needles are widely used in the health care industry. It has been estimated that there are over five billion needles used each year in the U.S. alone. Needles are used for a wide variety of purposes. Needles are used for drawing blood from a patient for analysis; giving injections or immunizations; removing fluid from the body for treatment, such as from the thoracic cavity, peritoneal cavity, a joint, or the chest; obtaining signal fluid for analysis; drawing medication into a syringe in preparation for administering the medication to a patient; taking samples of amniotic fluid for intrauterine studies of a fetus; etc.

The training, care and dexterity of the personnel who handle needles vary considerably. The person handling the needle may be a medical technician, a nurse, a doctor, or a patient administering insulin or other drug to himself. The training in proper handling of needles varies considerably from individual to individual, as does the awareness of the risk of a needle stick with a contaminated needle. The care taken to avoid an accidental needle stick to themselves or another person may vary considerably. An individual's manual dexterity will also vary widely from person to person and may change with the individual, depending on the situation. For example, during an emergency situation, a person's hand may be less steady or the person may be distracted while handling a needle. In addition to the risks to the technicians, nurses, patients, and doctors handling the needle, there are also risks to the janitorial staff who clean medical clinics and hospitals.

Accidental needle sticks to an individual occur in a variety of situations. One of the most common is when the user is recapping the needle with the cover after removing the needle from the patient. When recapping the needle, the user generally holds the syringe having the needle in one hand while holding the cover in the other hand and advances the cover towards the needle tip until the needle tip is covered by the cover. The risk is that, as the cover approaches the needle, a slight misalignment or unexpected movement of either the needle or the cover will cause the fingers or hand holding the cover to be punctured by the needle. Even a person having a steady hand may stick himself if inadvertently bumped or in a situation where the patient is uncooperative. Needle sticks may also occur when using the needle to inject blood or other fluid removed from a patient into a test tube for later testing, to draw medicine from a bottle, to insert medication into an intravenous line for an injection, or other assorted uses of the needle.

The problem posed by being stuck with a needle is the possibility that the needle is contaminated. Blood is well known to carry a variety of infectious agents which can be spread by a needle stick from a needle which has just been used in a person having an infection. These infections include: HIV (the agent of AIDS); Hepatitis B (serum hepatitis); Hepatitis Non A Non B; Delta Hepatitis; Cytomegalovirus (CMV); and a variety of other infectious agents. Unfortunately, only a small stick with a contaminated needle may be sufficient to transmit many types of infection.

The magnitude of the risk is somewhat difficult to determine. In many hospitals, all accidental needle sticks are requested to be reported. However, personnel often tend to under-report accidental needle sticks because they are too busy, are too embarrassed to report having stuck themselves, a patient or a fellow health worker, or forget to report due to the emergency of the situation at the time. Some studies estimate that there are as many as 120 or 160 accidental needle sticks per year per 1000 members of a hospital staff. It has been estimated that there are in excess of 80,000 accidental needle sticks each year in the U.S.

One solution to reduce the risk of accidental needle sticks is to place a Sharp's container in each room of a medical unit. A Sharp's container is a puncture-proof container into which the needle is placed which encloses the needle entirely and may also break it off. The Sharp's container prevents the needle from being removed after it is placed therein. The container is then disposed of in its entirety. When a Sharp's container is present in the room, the user is cautioned to not recap the needle at any time. This is because it is felt that the greatest risk of an accidental needle stick occurs when recapping a contaminated needle, as previously explained herein. Rather, the user is instructed to simply dispose of the exposed needle into the Sharp's container.

Unfortunately, this solution has numerous disadvantages and does not prevent numerous needle sticks. A Sharp's container must be located in each individual medical unit or room and must be close to the place where the needles are being used. Otherwise, the needle user must move with the uncovered needle from his present position near the patient to the Sharp's container. This creates significant additional risks.

Even with properly located Sharp's containers, placing the contaminated needle in a Sharp's container is not immediately possible in many situations. The needle user may be caring for the patient from whom the needle was just withdrawn by applying pressure with one hand to the point where the needle was removed to prevent bleeding. In the event the patient is a young person or a person particularly disturbed by the sight of a needle being placed in or removed from his body, additional risk occurs because of the possibility of unexpected movement of the patient. If the needle has been used to aid in the placement of an intravenous ("IV") tube, the user must do many things at once which limit the opportunities to dispose of the needle. For example, blood may be coming back up the catheter which was inserted over the needle. If the user leaves the patient, the blood may leak out of the catheter or the IV may come out of the patient's arm. Often, the user places the contaminated needle on a table next to the patient while completing the medical procedure and further caring for the patient. The contaminated needle is disposed of when he has time. This leaves an uncovered, contaminated needle in an environment where the type of activity is occurring which may result in accidental needle sticks. The Sharp's box can also be full, thereby presenting a problem with needle disposal.

A different set of problems are present when it is necessary for the needle to be reused. For example, blood or other fluid is often drawn from a patient for use in diagnostic tests. In this procedure, a needle attached to a syringe is placed into the patient's body and the syringe is filled with the body fluid to be tested. The needle is removed from the patient's body with the syringe full of the extracted fluid to be tested. The needle is now contaminated and the syringe is full of contaminated fluid. Frequently, numerous tests are to be performed which require a specific amount of the body fluid to be placed in different test tubes. The hospital staff member, after removing the needle from the person's body, sticks the needle attached to the syringe having the fluid therein through a rubber covering over a test tube and places the required amount of fluid into the test tube. Movement similar to that used in placing the cover of the needle is involved, with similar risks. The needle is then removed from this test tube and the same needle is used to place a fluid sample into a second test tube. Numerous test tubes may have varying amounts of the body fluid placed therein by the hospital staff member immediately after having drawn the fluid from the patient. This presents numerous opportunities for the hospital staff member to accidentally stick himself with the contaminated needle. A similar problem occurs when connecting one IV line to a second IV using a needle to make the connection or when drawing medicine from a bottle. For those procedures which require the same needle to be used repeatedly after it has been removed from a patient's body, a Sharp's container is not a possible solution until after the high risk, repeated uses of the needle have been completed.

SUMMARY OF THE INVENTION

It is therefore an object of this invention to provide a puncture-proof member for covering the sharp tip of a needle after it has been used on a patient.

It is an object of this invention to provide a method of cupping the sharp tip of a needle using a movement which significantly decreases the likelihood of an accidental needle stick.

It is another object of this invention to provide a method of capping a needle which permits the needle to be capped using the same motion as used in removing the needle from the patient's body.

It is another object of this invention to provide a recessed needle coupled to a syringe for reducing the risk of an accidental needle stick.

It is another object of this invention to provide a safety device that will permanently cap the needle after it has been uncapped a single time.

These and other objects of the invention, as explained herein, are accomplished by providing a sleeve around the needle. The sleeve slides from the base of the needle to the tip. A puncture-proof blocking member shaped to mate with the end of the sleeve is coupled to a cord extending through the sleeve. When the sleeve reaches the tip, the distal end of the sleeve engages the blocking member in a locking relationship. The tip of the needle is now surrounded by a puncture-proof member and may be safely disposed of. The invention may also include an over-cover which is permanently locked to the hub of the needle, after which the needle may be removed from the syringe and disposed of. A tandem, recessed needle may be provided underneath the needle which was used to extract fluid from a patient. The tandem needle is recessed below a protective wall to reduce the possibility of an accidental stick therewith. The contaminated needle is removed and discarded, permitting the recessed needle to be used.

DETAILED DESCRIPTION OF THE INVENTION

Figures 1, 2:
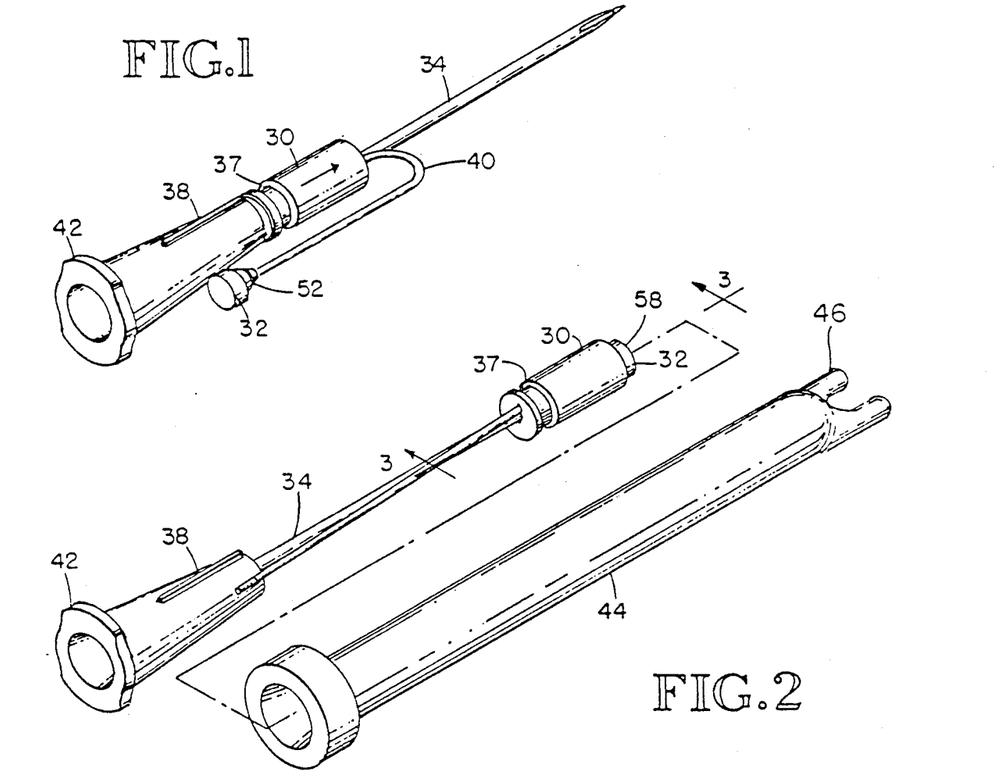
FIG. 1 is an isometric view of the protective capping system of the invention, with the needle exposed.
FIG. 2 is an isometric view of the protective capping system of FIG. 1, with the needle covered, and an over-cover ready for use.

A needle 34 having a sleeve 30 circumferentially mounted thereon is shown in FIG. 1. Further illustrated in FIGS. 3 and 5, the sleeve 30 includes an interior shaft 36 having a diameter greater than the diameter of the needle 34. As illustrated in FIG. 1, the needle 34 is mounted on a hub 38 using methods well known in the industry. A cord 40 is attached to the hub 38 at one of its ends and secured to a puncture-proof blocking member 32 at its other end. The cord 40 extends through the shaft 36. Alternatively, the cord 40 may extend through a separate shaft in sleeve 30. The hub 38 includes an industry standard Luer flange 42 for attachment to a syringe as is known in the industry. An over-cover 44 having a forked member 46 at its top is placed over the needle 34 and hub 38. The sleeve 30 is equal or slightly less in diameter than the hub, thus permitting the over-cover 44 that would be used in the prior art with the hub 38 to be placed over the needle assembly with the sleeve and blocking member in a standard fashion.

Figure 3:
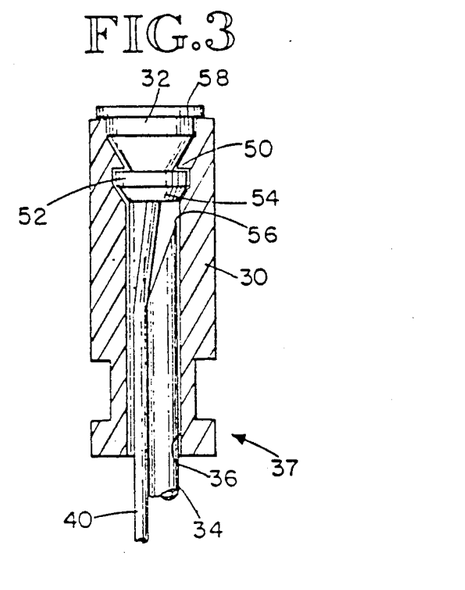
FIG. 3 is an enlarged cross-sectional view of the protective capping system.

A cross-sectional view of the sleeve 30 in the locked position at the tip of the needle 34 is illustrated in FIG. 3. An annular flange 50 is formed on an interior surface of the sleeve 30. The puncture-proof blocking member 32 includes a lug region 52 engaging the interior flange 50 of the sleeve 30. The blocking member 32 includes a bottom region 54 which is adjacent the tip 56 of the needle 34. The flange 50 of the sleeve 30 holds the blocking member 32 in a locked relationship with respect to the sleeve and the needle. The blocking member 32 includes a top region 58 extending above and overlying the end of the sleeve 30, as shown in FIGS. 2 and 3. In the event pressure is applied to the and of the sleeve assembly, the force is applied directly to the blocking member 32.

The blocking member 32 is puncture-proof to prevent the point of the needle 34 from penetrating through the blocking member 32. If the needle accidentally strikes a person, the sharp tip 56 is covered and the skin of the person will not contact the tip 56 and thus will not be penetrated. The blunt cover 32 will strike the person, not the sharp tip 56. If sufficient pressure is applied to the blocking member 32, the tip 56 of the needle 34 will be dulled or embedded in the blocking member 32. After the needle is embedded in the blocking member 32, the tip is permanently covered and does not pose a risk.

The cord 40, which couples the blocking member 32 to the hub 38, is made of an extremely strong material, such as a monofilament fiber. Fibers of this type are presently used to attach tags to various articles of clothing and are extremely rugged. The cord 40 is a predetermined length and relatively inelastic. The blocking member 32 extends just beyond the tip 56 of the needle 34 when the cord 40 is fully extended along the length of the needle 34, as shown in FIGS. 2-5. The cord 40 may bend back towards to the hub, as shown in FIG. 1, when the needle is being used. A bend may be pre-stressed into the cord 40 so that it springs back next to the hub 38 when the cover 44 is not in place.

Figures 19, 20, 21, 22, 23:
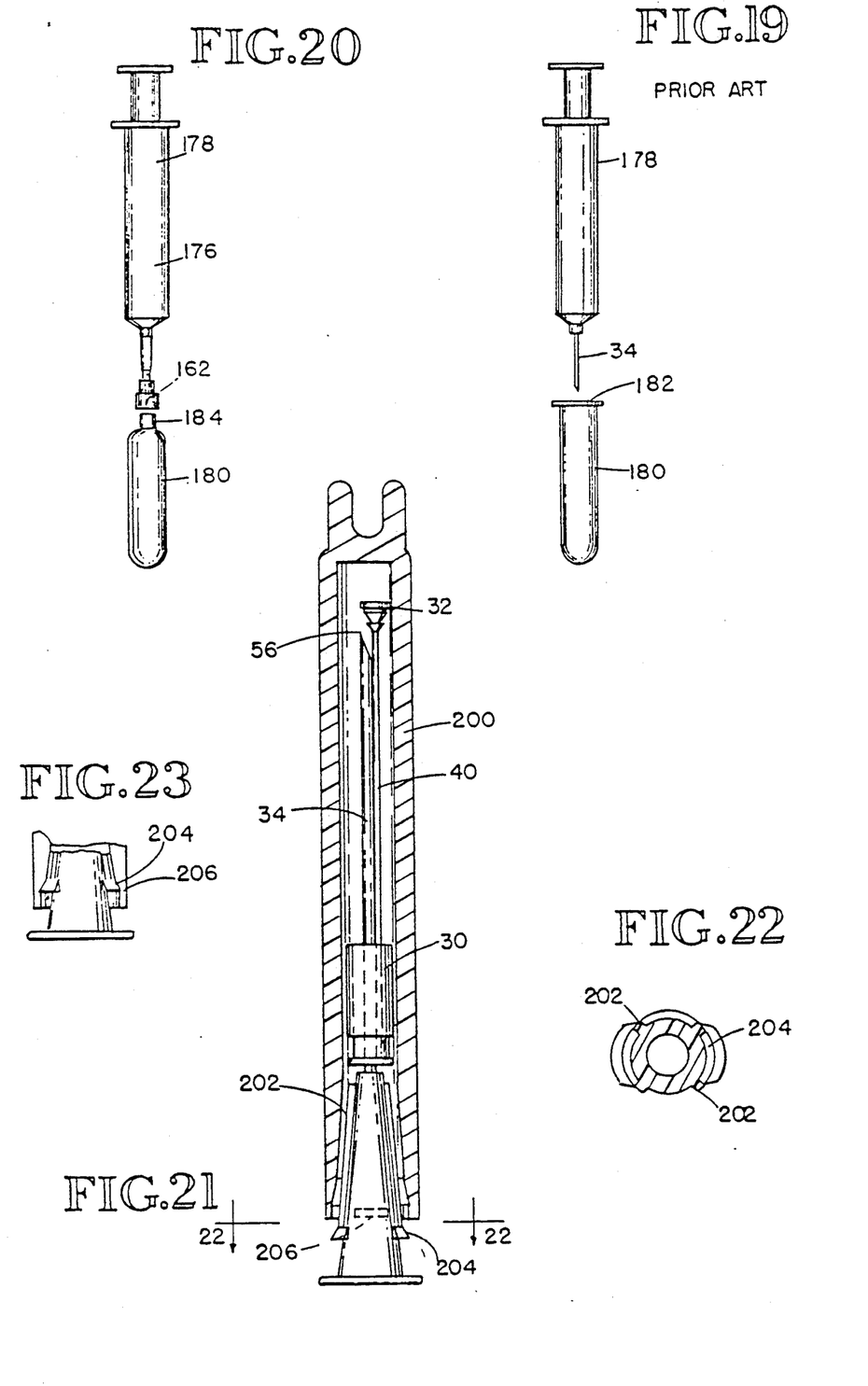
FIG. 19 is a side elevation of a prior art needle for placing a fluid from a patient into a container using a contaminated needle.
FIG. 20 is a side elevation of the recessed needle of the present invention of FIG. 16 used for placing a fluid removed from a patient into a test tube.
FIG. 21 is a partial cross section of a safety over-cap retaining device.
FIG. 22 is a cross-sectional view taken along lines 22—22 of FIG. 18.
FIG. 23 is a cross-sectional view of the safety cap and hub at FIG. 21 with the safety cap locked into position.

The method of using the needle safety devices as illustrated in FIGS. 1-3 is as follows. The protective over-cover 44 is placed over the needle and sleeve assembly by the manufacturer. When the protective over-cover 44 is in position, as shown in FIG. 21, the cord 40 extends along the length of needle 34, with the blocking member 32 just beyond the tip of the needle, as shown in FIG. 21. The sleeve 30 is at the base of the needle adjacent the hub, as shown in FIG. 1. When the needle is ready for use, the protective cover 44 is removed, thereby allowing the blocking member 32 to spring out of the way from alongside the needle 34 and into a position adjacent the hub 38 due to the preformed spring-biasing of the cord 40, as shown in FIG. 1.

The needle is then used for its intended purpose, namely, to draw blood or some other fluid from a patient, to inject a fluid into a patient, or any of the other uses described herein. In the prior art, after the needle has been placed into the patient but just prior to removing it from the patient's body, the person using the needle places an absorbent material, such as gauze or a cotton ball, over the puncture location in the skin through which the needle was placed. In a needle having the inventive sleeve 30 thereon, in the same grip of the fingers which is holding the absorbent material, the person using the needle also grips the sleeve 30. The needle is then retracted in a usual manner from the patient's body. As the needle is retracted, the sleeve 30 slides along the needle 34 and draws the cord 40 adjacent the needle. As the tip of the needle emerges from the patient's skin, the sleeve 30 comes adjacent the tip 56 of the needle. The blocking member 32 is also drawn by cord 40 into a position adjacent the tip 56 of the needle 34. The person then slides the sleeve 30 a short distance further to solidly lock the blocking member 32 into the sleeve 30. A distinctive "click" is heard as the lug 52 passes over and engages the flange 50. 35. The person using the needle is then assured that the sleeve has completely and properly engaged the blocking member 32 in a locked relationship, as shown in FIG. 3. The sharp tip 56 is now surrounded by puncture-proof members. The sleeve 30 and blocking member 32 may be made of a plastic, hard rubber, thin metal, or other slightly resilient material permitting slight flexing or bending in the upper region to permit flange 50 to engage lug 52 and provide the distinctive "click." The person using the needle may now place it on a table or other location and administer to the needs of the patient. At a convenient time, the cover 44 is placed over the protected needle and the needle is disposed of.

An alternative method of covering the needle is to first completely withdraw the needle from the patient's skin. Then, firmly gripping sleeve 30 at rear portion 37, slide it along needle 34 toward tip 56 until blocking member 32 swings into position just above the tip of the needle and solidly engages the interior surface of the sleeve 30 until the distinctive "click" is heard which assures the user that the needle is properly and permanently protected, as shown in FIG. 3.

An alternative method of covering the needle is by using forked member 46 on the end of over-cover 44 to slide the sleeve 30. This provides an additional safety feature in capping the needle. The forked member 46 is of such a dimension that it fits snugly into recess 37 of sleeve 30. According to this method, the user holds the cover 44 in one hand and the syringe having the contaminated needle in the other hand. The user then places the forked region 46 into the recess region 37 and slides the sleeve 30 towards the tip of the needle 34 until the distinctive "click" is heard, which assures him that the needle is covered. This permits the user to maintain a safer distance from the needle.

A significant advantage of each of the methods of covering the needle is that the needle is covered by a movement from the base to the tip rather than by approaching from the sharp tip. Gripping the rear portion 37 of sleeve 30 and moving it forward draws the cord 40 along the needle to bring the blocking member 32 over the tip of the needle, with the user's hands remaining behind the tip of the needle. The needle tip 56 is thus covered and capped with a movement from the rear of the needle forward and is covered before the user's hands can reach the tip 56. The blocking member 32 is pulled into position above the sharp point 56 and locked into position while the user's fingers are still on the sleeve 30 and have not yet reached the sharp tip. This prevents the fingers of the user from being accidentally stuck with the needle. Use of the forked end of the over-cover provides another layer of protection to permit the user's fingers to remain away from the needle tip until it is covered.

Should a sudden movement or unsteadiness occur, the user's hand is moving from the base upward rather than towards the sharp tip 56. If the user's hand slips off sleeve 30, the hand will go past the needle tip 56 without the risk of striking the sharp tip. The hand will continue to move away from the sharp tip after the slip and become further separated from the needle. The user may then once again place his hand, coming from behind the needle, at the hub 38 near the base of the needle, engage sleeve 30 and slide it to the tip 56, as previously attempted.

In the prior art method of capping a needle, if a slip caused the cover 44 to miss the needle, the fingers of the user gripping the cover were approaching the sharp tip and were at risk of being stuck. Even if the fingers holding the cover missed the sharp tip, the other fingers, the rest of the hand and arm were all approaching the sharp tip 56 and each were at risk of being stuck. According to the present invention, this problem is avoided.

The needle tip 56, generally the only part of the needle capable of penetrating a person's skin, is completely surrounded and isolated by puncture-proof members that are not movable in any direction. The blocking member 32 is positioned directly over and adjacent the tip 56 of the needle. Should pressure inadvertently be applied to the needle, the blocking member 32 completely covers the tip of the needle while the sleeve 30 surrounds the needle to prevent the sharp tip 56 from being exposed. If sufficient pressure is applied, the sharp tip 56 will be bent and dulled or needle 34 may embed itself in the blocking member 32, thus making it very difficult for a person to be stuck with the needle 34. In the event pressure is applied to the sleeve 30 to force it upward and over the tip of the needle 34, the cord 40 holds the blocking member 32 firmly in position, which blocks further movement of sleeve 30. The cord 40 is of an extremely strong material which does not exhibit elastic qualities or elongation when placed in tension. The sleeve 30 may not be forced off the tip of the needle even if a great amount of force is applied. Pulling sleeve 30 back down towards the hub 38 brings the blocking member 32 into contact with tip 56, which prevents further movement of sleeve 30 because flange 50 engages lug 52. Both the sleeve 30 and blocking member 32 are locked in position.

Figure 3A:
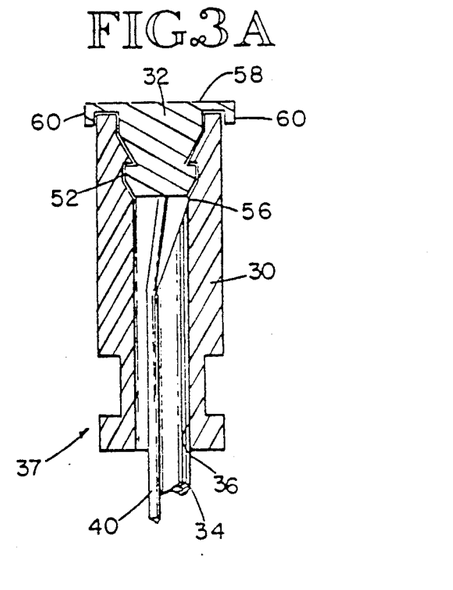
FIG. 3a is an enlarged, cross-sectional view of an alternative embodiment of a protective capping system.

The distal end of the sleeve 30 may be made of a plurality of different shapes according to the desired locking features or reusable requirements of the needle. The blocking member 32 may also be made a plurality of different shapes or materials to provide additional protection or to mate appropriately with the interior surface of the sleeve 30. For example, the blocking member 32 having a top region 58 may have an exterior annular flange 60 extending around the outer edges of the sleeve 30, as shown in FIG. 3A. This provides additional safety to ensure that the blocking member 32 cannot be removed from the sleeve 30 by pressure either from the side, top or bottom.

Figures 4, 5, 5A:
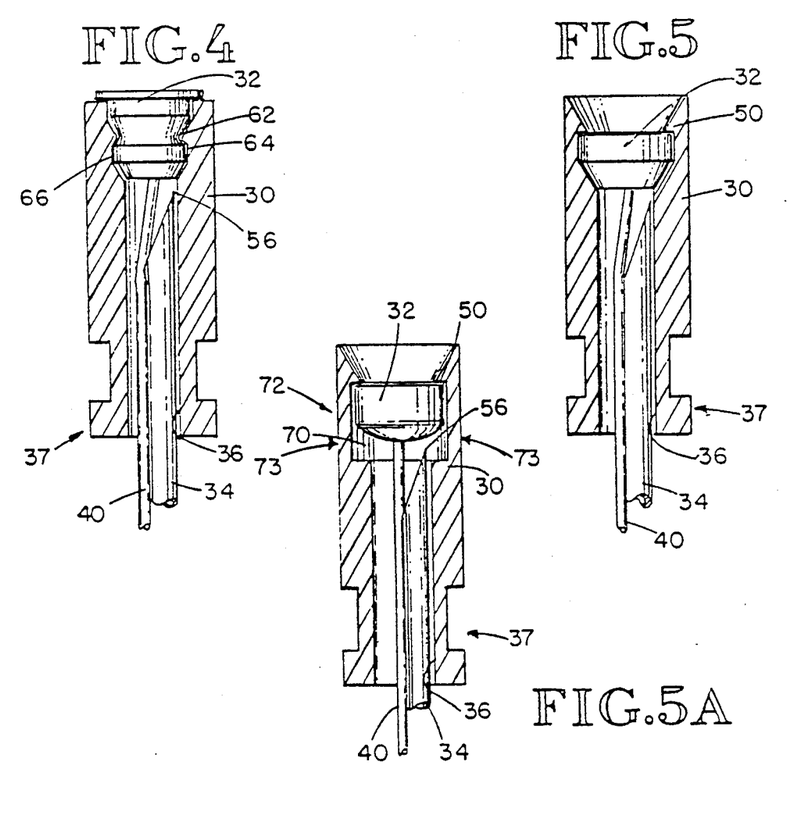
FIG. 4 is a cross-sectional view an alternative embodiment of the protective capping system.
FIG. 5 is a cross-sectional view of an alternative embodiment of the protective capping system.
FIG. 5a is an alternative embodiment permitting reuse of a needle using the protective capping system.

An alternative embodiment of the interior surface of the sleeve 30 and the blocking member 32 permits the blocking member to be removed, if desired, as shown in FIG. 4. The interior surface of the sleeve 30 includes a protrusion 62 which resiliently engages the blocking member 32. The blocking member 32 similarly includes a protrusion 64 which resiliently engages a recessed region 66 on the FIG. 4. interior surface of the sleeve 30, as shown in FIG. 4. The sleeve 30 may be pulled downward with protrusion 62 being resiliently biased outward away from the protrusion 64 of the blocking member 32, thus permitting the blocking member 32 to move away from the position adjacent to tip 56 of the needle 34. The needle may then be used again, such as to place the fluid which has been withdrawn from the patient into a test tube or administer further medication, etc. The needle is uncovered for a second use by gripping the sleeve 30 and pulling downward. This keeps the user's fingers away from the sharp tip 56 after use. Sleeve 30 is then slid back into the protective position, with the blocking member 32 covering the tip of the needle.

An alternative locking member 32 and interior surface of the sleeve 30 are illustrated in FIG. 5. In this embodiment, the sleeve 30 slides completely over the blocking member 32 and the flange 50 locks over the top of the blocking member 32. In this embodiment, the sleeve 30 extends above the blocking member 32. Any pressure applied to the ends or sides of the sleeve 30 serve to press the flange 50 inward or downward against blocking member 32, thus, further protecting the needle and ensuring that it will not create an accidental puncture. A force applied in this region tends to make the needle more protected and less likely to injure a person rather than increase the risk of accidental needle stick as occurred in the prior art. The blocking mechanisms shown in FIGS. 3 and 3a provide similar protection by transferring force directly to the blocking member.

An alternative embodiment of a removable blocking member 32 to permit reuse of the needle of 34 is illustrated in FIG. 5a. In this embodiment, a void region 70 is left under the blocking member 32. pressure may be applied to resilient region 72, adjacent the void on the interior surface, as shown by the arrows 73 of FIG. 5a. This causes the flange 50 to bend outward and open to permit the blocking member 32 to exit from the flange 50. The flange 50 may be an annular flange or, alternatively, as shown in FIG. 5a, two flanges which extend only partially around the top edges of the sleeve 30. With the user applying force at the region 72 to release the blocking member 32, the sleeve 30 may be slid down towards the base of the needle, as shown in FIG. 1, and the needle may be reused, if required. However, with the design of FIG. 5a, if pressure is applied to only one side, the top or other regions of the sleeve 30, the blocking member 32 is held in position and the needle tip 56 remains encased to prevent accidental needle sticks.

The embodiments of the invention as shown in FIGS. 1-5a have significant safety and commercial advantages. The sleeve 30 and member 32 are generally made of a resilient and relatively inexpensive plastic material similar to the type of material used to make hub 38. Metal may be used, if desired. The shaft 36 is sized to permit the sleeve to slide smoothly up and down the needle. Further, the sleeve 30 has an outer diameter less than the diameter of the lower region of the hub 38. The standard sized over-cover 44 of the prior art may be used without requiring modification. The cord 40 is attached to the hub 38 using standard plastic cement, heat bonding or other known methods. The cord 40 may be an integral molded part with blocking member 32 or attached using through-hole drilling, plastic cement, heat bonding or other known methods. This invention may be easily attached to conventional needles and hubs. The flange 42 and hub 38 are industry standard in size and may be used on any syringe made according to industry standards. The protective device is thus not obtrusive and does not prevent efficient use of the sharp end of the needle for its intended purpose and yet effectively covers the needle immediately after being used. Thus the system can be used on any length needle.

Figure 27:
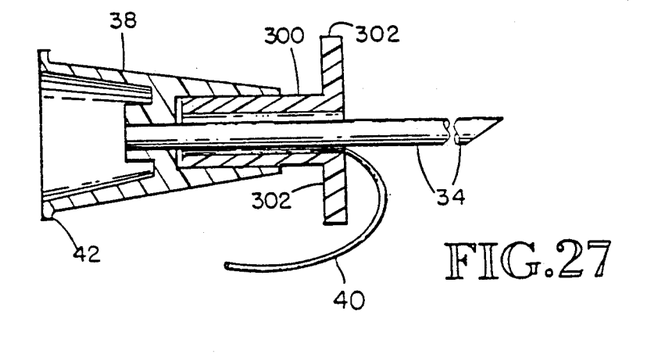
FIG. 27 is a cross-sectional view of a recessed sleeve assembly.

It may also be helpful to recess the sleeve in the hub 38 to provide a longer needle working length for any given device length (FIG. 27). This configuration also utilizes the sleeve to further support the needle 34 itself and may help prevent bending of the needle. A flange 302 is shown on the proximal end of the sleeve body 300 extending out of the hub 38 with sufficient distance to allow forked member 46 (FIG. 2) to engage the flange 302 similar to the use of the forked member to engage recess region 37, as previously described. The flange 302 can be made larger than would be required for engagement of the forked member 46 to act as a guard to provide additional protection for a person's fingers should the device be closed by hand without the forked member 46.

Figures 6, 7:
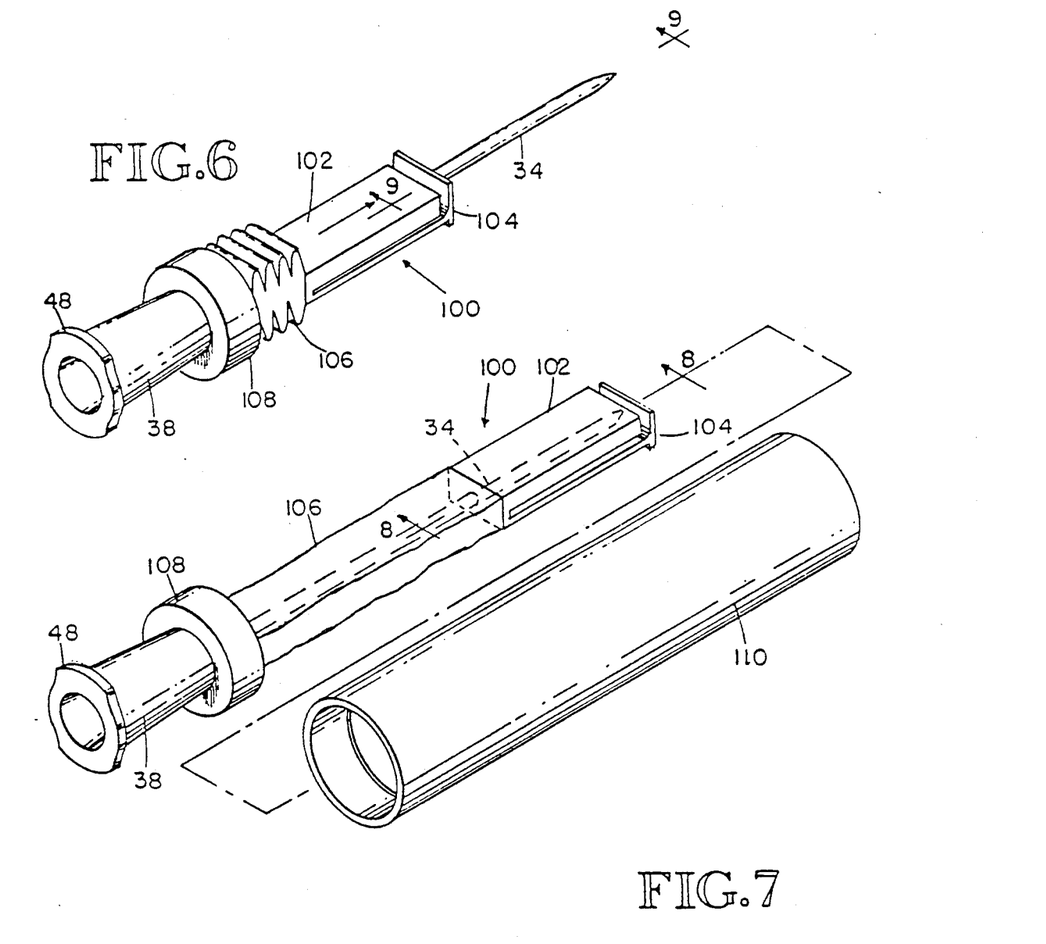
FIG. 6 is an isometric view of an alternative embodiment of a needle protection device with a sheath showing the needle exposed.
FIG. 7 is an isometric view of the needle protection device of FIG. 6 with the needle covered and a protective over-cover for placing in position.

A second needle stick prevention device is illustrated in FIGS. 6-10. A needle 34 mounted on a hub 38 similar to the needle of FIG. 1 has a needle protection device 100 coupled thereto. The needle protection device 100 includes a sleeve member 102 and a blocking member 104. A collapsible membrane 106 is coupled at one end thereof to the needle protection device 100 and at the other end thereof to the hub 38, as shown in FIG. 6. A collar 108 may be provided for coupling the over-cover 110 to the top of the hub; however, this is not required in the event the over-cover 110 is sized to resiliently couple the standard sized hub 38 similar to the over-cover 44 of FIG. 2. Use of the collar 108 permits the needle protection device 100 to be made larger than the diameter of the hub, which may be desired in some circumstances.

Figures 8, 9:
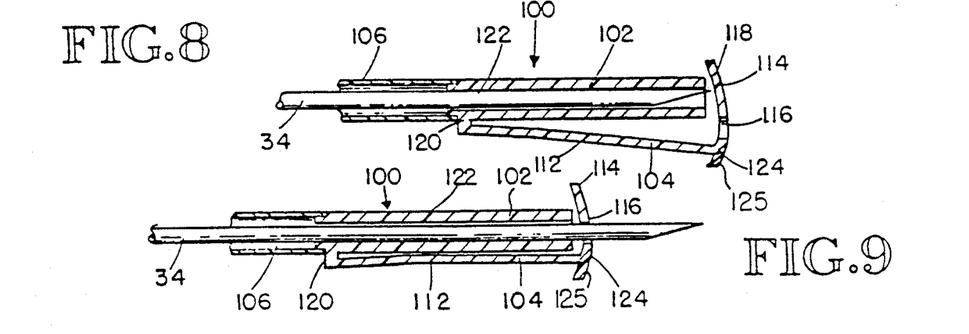
FIG. 8 is a cross-sectional view taken of an alternative embodiment of the protective cap system of FIG. 7.
FIG. 9 is a cross-sectional view of an alternative embodiment of the protective cap system as shown in FIG. 6.

Blocking member 104 is integrally coupled to the sleeve member 102, as shown in FIGS. 8 and 9. The blocking member 104 includes an arm portion 112 and a blocking portion 114. The blocking portion 114 includes a hole 116 having a diameter slightly larger than the external diameter of the needle 34. The blocking portion 114 extends completely across the front of the sleeve member 102 and includes a lip region 118 which overlaps the opposite side of sleeve member 102. The arm portion 112 extends from the needle protection device 100 at a base region 120, as shown in FIGS. 8 and 9.

The needle protection device 100 may be constructed using a material which is extremely hard, yet resilient and flexible in one dimension. A hard plastic is a suitable material for making the protective device 100. The plastic is preferably clear, so that the user may see the needle shaft and tip 56 at all times; however, it may be made of translucent or opaque material if desired. The blocking portion 114 is puncture-proof so that the sharp tip 56 of the needle 34 will not penetrate the material. The needle is stopped from further movement upon abutting against the blocking portion 114.

The method of using the needle protection device is illustrated in FIGS. 6-9 and is as follows. The needle, as shipped by the manufacturer, may be either completely covered, as shown in FIG. 7, or the needle protection device may be retracted with the sharp needle tip exposed, as shown in FIG. 6. The sheath 106 is a sterile membrane and ensures that all portions of the needle remain sterile at all times, so long as it is properly covered.

Assuming the needle shipped by the manufacturer is completely covered by the needle protection device, as illustrated in FIG. 7, the user must first uncover the needle before using it. The user uncovers the needle by placing their thumb against the sleeve portion 102 and their finger against the arm portion 112 of the blocking member 104. The user then squeezes his thumb and fingers together to bring the arm 112 against the sleeve 102, as shown in FIG. 9, to align the hole 116 with the hole 122 extending through the sleeve 102 and sliding the needle protection device 100 down the shaft of the needle towards the hub 38. The extending lip portion 118 provides an additional safety stop to ensure that the user's hand is properly placed to avoid accidental needle sticks. Specifically, if the user's thumb is extending above the tip of the needle, the lip portion 118 will contact the thumb, preventing movement of blocking portion 114. The user must move his thumb below the lip portion 118 of the blocking portion 114 in order to align the hole 116 with the needle. The entire hand must always be behind the sharp tip 56 before it can be exposed. This ensures that all parts of the person's hand are below the tip of the needle at the time the needle is exposed If any portion of the person's thumb or finger overlaps the lip as it is pressed relative to the sleeve 102, the user will not be able to align the holes or will recognize that his hand is in the wrong position and will move his hand down the needle protection device below the tip of the needle before aligning the holes and exposing the needle. Similarly, if a portion of the user's finger extends above the curved portion 124, the pressure will be applied partially downward, making it difficult to move the arm member 112 to align the holes. The thumb and the finger must be approximately across from each other to press the member 112 to align the holes. If the finger is misaligned with the thumb, such as by being closer to the tip 56, the needle will pivot when pressure is applied rather than aligning the holes 116 and 122. This ensures that the user, when uncovering the needle, is not punctured by the needle. Alternatively, the blocking member 104 may include a flange 125 extending from the curved portion 124 acting as a guard to ensure that the user's hand does not extend past the end, as shown in FIGS. 8 and 9. While exposure of the needle has been described with respect to having the thumb on the sleeve portion and the finger on the arm portion 112, it is to be understood that the positions may be reversed or other methods or means may be used to press the arm portion 112 towards the sleeve 102 to align the hole 116 with the tip of the needle.

The membrane 106 completely surrounds the needle 34 and is coupled in a sealed relationship around the base of the needle protection device 100. The membrane 106 is a collapsible membrane and may be made from plastic, cloth or other collapsible material. However, the membrane 106 is not elastic or stretchable and can withstand considerable force in tension. The membrane 106 ensures that the needle protection device 100 does not slide off the end of the needle to leave the needle exposed, similar to the function provided by cord 40.

Figure 2A:
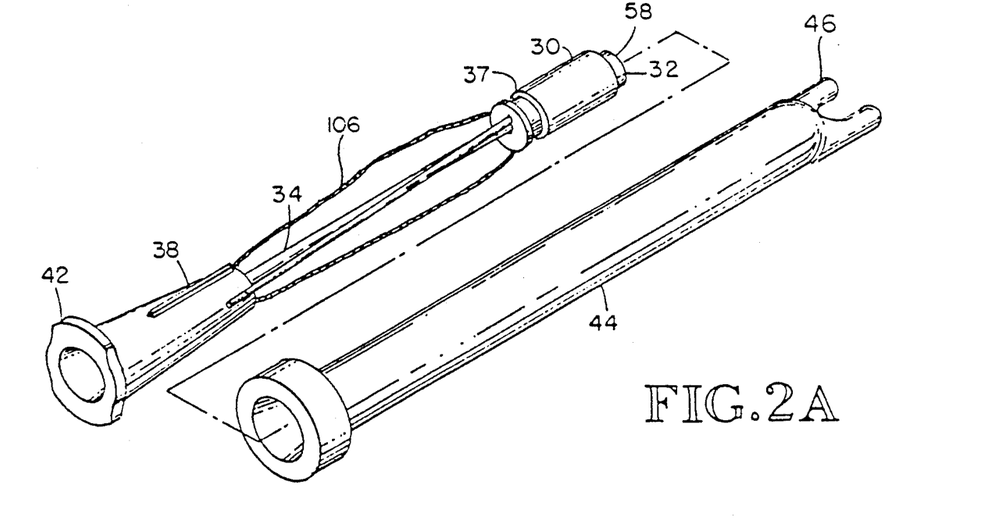
FIG. 2A is an isometric view of an alterative embodiment of the protective capping system of FIG. 1, having a flexible membrane coupled between said sleeve and said hub and extending around the needle.

FIG. 2A illustrates an embodiment having the collapsible membrane 106 coupled between the hug 38 and the sleeve 30. The function and operation of the membrane 106 is identical to that previously described with respect to FIGS. 6-9.

After the needle has been used, such as for removing blood or other fluid from the patient, giving medication or removing medication from a bottle, the needle protection device 100 is slid from the hub 38 near the base of the needle to the top until the tip of the needle 34 is withdrawn from the hole 116. The arm portion 112, being resiliently biased outward, springs away from the member 102 to remove hole 116 from alignment and to place blocking member 114 over the sharp tip of the needle to prevent accidental needle sticks. The membrane 106 completely covers the needle so that the entire needle is enclosed and isolated from the environment. Contamination to an open wound by contacting the side of the needle will not occur with sheath 106 in place. The needle may now be disposed of, either by placement in a conventional trash can, in a Sharp's container or recapping with cover 110 and then disposing of the needle.

Alternatively, it may be desirable to use the needle a second or third time, such as for placing the fluid removed from the patient into various test tubes so that analytical testing may be performed on the fluid. The needle protection device 100 permits repeated use of the same needle while providing the desired protection against accidental needle sticks. The user squeezes the sleeve 102 and arm portion 112, as previously described, to align the hole 116, and may reuse the needle as desired. The needle is covered between each use and covered just prior to disposing of the needle.

The needle may be capped while removing the needle from a patient's body, described with respect to capping the needle using the protection device of FIG. 1. For example, when the user places a piece of cotton over the point of entry into the body, the user may contact the lip 118 or sides of the needle protection device 100. As the syringe is pulled backwards to slide the needle out of the person's body, the needle protection device 100 slides up the shaft of the needle so that immediately upon removal from the person's body, the blocking member 114 springs backward and the needle is covered. The user may perform the necessary care on the patient and be assured that the needle is protected and will not cause accidental needle sticks until it can be properly disposed of.

Figures 10, 15:
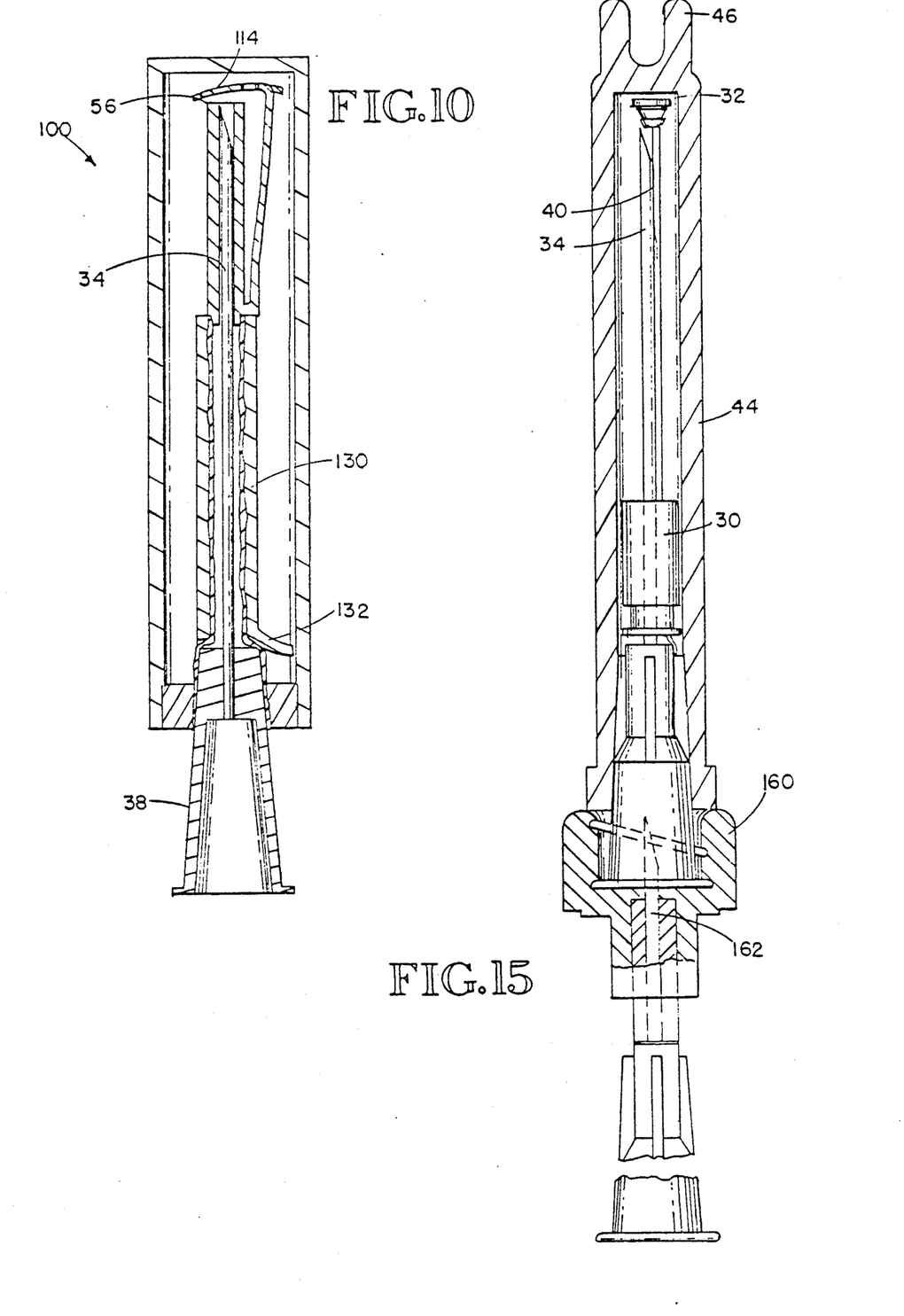
FIG. 10 is a cross-sectional view of a support member used with the needle safety device of FIG. 6 to prevent dulling the needle.
FIG. 15 is a partial cross-sectional view of a single-use needle having the needle protection device and a multi-use needle mounted in tandem on the same syringe.

A stand 130 for needle protection device 100 is illustrated in FIG. 10. As previously stated, the needle may be shipped with the needle protection device 100 covering the tip of the needle, as shown in FIG. 7. In the event the needle is shipped with the needle protection device covering the tip of the needle, it is possible that the sharp tip 56 of needle 34 may bump against the blocking member 114 while in transit, and thus dull the needle, causing discomfort when used on a patient. A protective stand 130 which abuts against the lower region of the needle protection device 100 and also abuts against the hub 38 may be used to ensure that the blocking member 114 is held above the sharp tip 56 of the needle 34. The stand 130 may be made of a rubber or bendable material having a slit down the length thereof to permit it to be placed around the compressible membrane 106 and be stiff to hold the member 100 in a spaced relationship away from the hub 38. The collar 130 has a tab portion 132 which the user may grip and pull towards him to remove the stand 130 from the needle prior to using.

Figure 13:
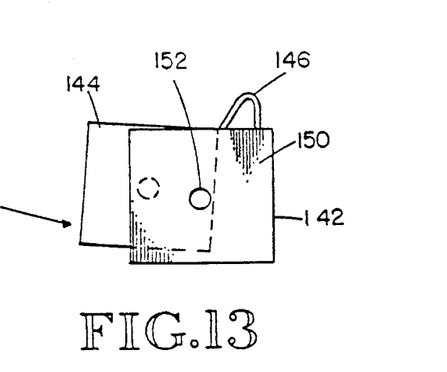
FIG. 13 is a top plan of the needle protection device of FIG. 11.
Figure 14:
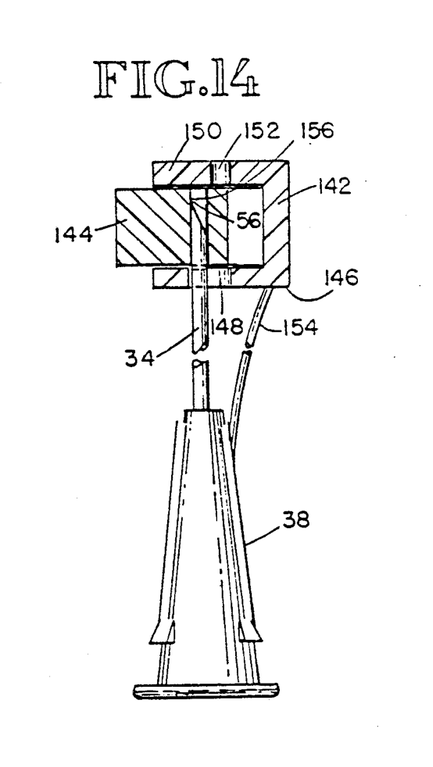
FIG. 14 is a partial cross-sectional view of the needle protection device of FIG. 11 in place on the needle.

An alternative needle protection device 140 is illustrated in FIGS. 11-14. The needle protection device 140 includes a rigid shell member 142 and an inner member 144. The member 144 is attached to a flexible strap 146 which is spring-biased outward to hold the member 144 and the shell member 142 in the nonaligned position, as shown in FIGS. 11-14. The bottom portion 147 of shell member 142 has a slot 148 therethrough. The top member 150 has a hole 152 therethrough. The diameter of the hole 152 is slightly larger than the external diameter of the needle which is to pass therethrough. A cord 154 is attached at one thereof to the bottom portion 146 of the shell 142 and at the other end thereof to the hub of the needle, as shown in FIG. 14, similar to the cord 40 of FIG. 1. The needle 34 extends through the slot 148 and partially into member 144 through shaft 156, as shown in FIG. 14. The hole 152 is not aligned with the shaft 156 and thus the upper surface 150 of the shell member 42 prevents the sharp tip of the needle from extending out of the member 144. The entire needle tip is covered and thus prevents accidental needle slicks. When a user is ready to use the needle, he presses the member 144 and the shell 142 together between his thumb and finger, overcoming the resilient bias of strap 146 to align the shaft 156 with the hole 152, as shown in FIGS. 13 and 14. The needle protection device 140 may then be slid down the shaft of the needle 34 to expose the sharp tip of the needle. The needle may then be used and covered after being used, as has been described with respect to the needle protection devices of FIGS. 1 and 6. The shell member 142 is made of a puncture-proof material which is not penetrable by the sharp tip 56 of a needle. This prevents accidental needle sticks from occurring when the needle protection device 140 is in place.

Figure 11:
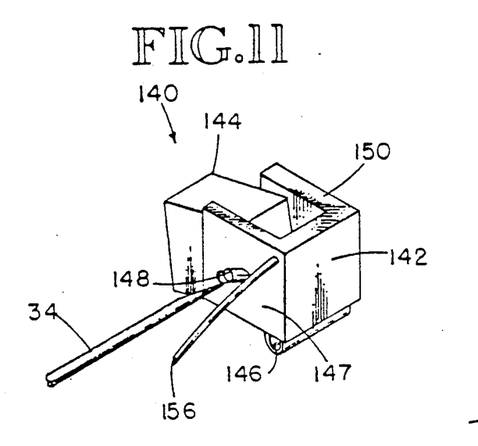
FIG. 11 is an isometric view of an alternative needle protective device.
Figure 12:
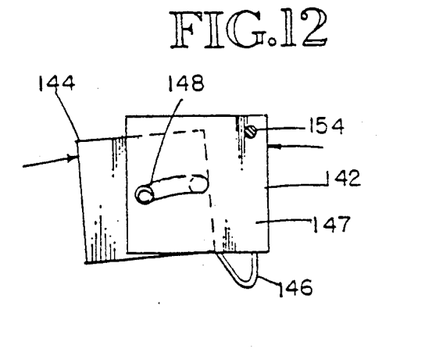
FIG. 12 is a bottom plan view of the needle protection device of FIG. 11.

The collapsible, protective membrane 106 shown in the embodiment of FIGS. 6 and 7 may also be attached to the needle safety devices of FIGS. 1 and 11.

A tandem needle arrangement having the second needle recessed is illustrated in FIG. 15. The needle protective device of FIG. 1 having the sleeve 30 and blocking member 32 is shown mounted above the recessed needle member, though any other needles illustrated herein or prior art needle assemblies may be similarly mounted. The recessed needle assembly includes a needle 162 and protective outer wall 160 having a top region 164 extending above the needle. Preferably, the interior of wall 160 includes an annular thread 163 of a standard Luer design as is used on syringes in the industry such that any standard needle or standard Luer flange may be placed therein. Alternatively, the interior of safety wall 160 may be another shape which engages hub flange 42 of hub 38. The hub 168 has a standard Luer lock flange 170 on the other end thereof for coupling to syringes of industry standard design.

Figures 16, 17:
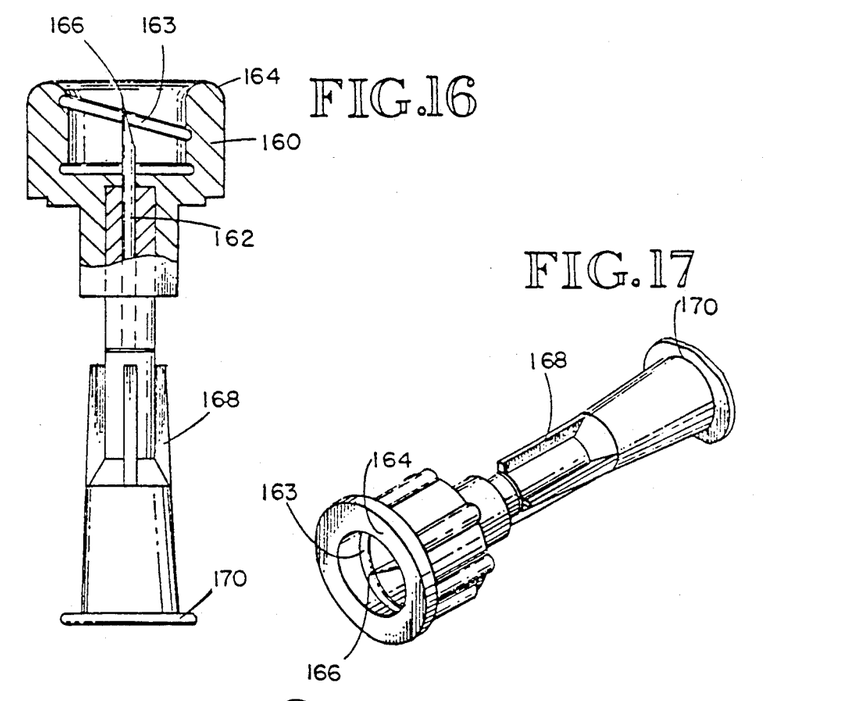
FIG. 16 is a partial cross-sectional view of the recessed needle and wall.
FIG. 17 is an isometric view of the recessed needle of FIG. 16.

The recessed needle assembly includes a recessed needle 162, as shown in FIGS. 15-17. The tip 166 of the recessed needle is placed sufficiently below the upper edge 164 of protective wall 160 to ensure that if a person's finger is placed over the top of the wall 160 the finger will not contact the tip 166 of needle 162. The standard size Luer lock as used in the industry has a smaller inside diameter than a person's finger. Thus, as a finger or other body part approaches the needle, it will abut the top region 164 of walls 160 and be stopped before striking the tip 166 of needle 162. Alternatively, a protective wall 160 having a smaller diameter may be used if additional protection is desired.

The recessed needle is designed to be used for all uses of the needle not requiring penetrating the skin of a person. For those uses in which the skin of a person must be penetrated, such as to remove the fluid from a patient's body or give medication, a first needle assembly, such as shown in FIGS. 1-3, is positioned above the recessed needle 162, as shown in FIG. 15. After the needle 34 has been removed from the patient's body, the needle is covered, preferably using the permanent covering described with respect to FIGS. 1-3 herein, and then disposed of. The recessed needle 162, while containing on an interior surface the contaminated fluid, has not come into contact with the patient's body. Further, the needle tip 166 is recessed below the top region 164 of protective wall 160 to ensure that the sharp tip does not accidentally stick a person and expose them to the contaminated fluid contained within the needle or the syringe to which the needle is attached. The recessed needle 162 may then be used in conjunction with the syringe to remove fluid from any system or container, such as a medicine bottle, IV system, used to draw fluid from a patient, take a sample of the IV fluid, etc., or to place the fluid in any system or container, test tube, IV system, etc.

Figure 18:
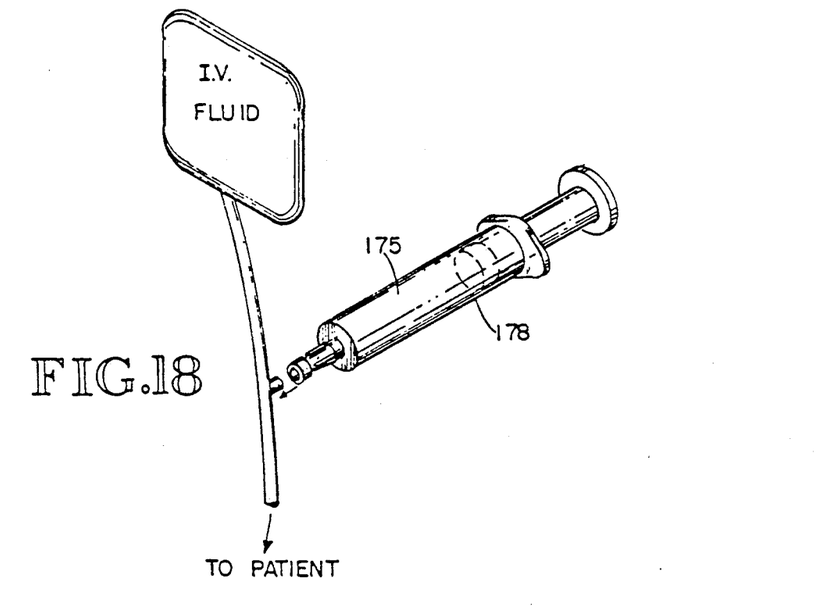
FIG. 18 is a side elevation showing the recessed needle in use for an injection into an IV.

Examples of uses of the recessed needle assembly and mating receptacles are illustrated in FIGS. 18-20. The recessed needle assembly may be used, for example, in placing a fluid into an intravenous system going to a patient's body. According to the prior art, an exposed needle, similar to that shown in FIG. 19, is used for inserting a fluid into an IV system. Use of the recessed needle system of this invention decreases the likelihood of an accidental needle stick.

A prior art method of placing a fluid just removed from a patient's body into test tube 180 or removing medication from a bottle is illustrated in FIG. 19. According to the prior art, a sharp needle is used to penetrate a rubber member 182 and the fluid is then injected into the test tube, or alternatively, medication removed from the bottle. In the event the syringe 178 contains a fluid recently removed from a person's body and the needle 34 is a contaminated needle, the user faces an increased risk of accidental needle stick and exposure to infection using the prior art method.

Use of the recessed needle assembly of the invention is illustrated in FIG. 20. The needle which was used to remove the fluid from the patient's body was mounted in tandem above the recessed needle, as shown in FIG. 15, and has since been removed from the syringe, properly covered and disposed of. The test tube 180 preferably has a mating rubber-covered opening 184 which the protective cover 160 may go over and permit the recessed needle 162 to penetrate the rubber membrane and insert the fluid into the test tube 180. The test tube 180 may be open to the atmosphere when inserting the fluid and later sealed, or may be under vacuum and "draw" the fluid in, as is known in the industry. The protective wall 160 ensures that the user is shielded from the sharp tip 166 of the needle 162 and thus is not accidentally stuck with the needle attached to a syringe containing contaminated fluid. Should a slip occur, the wall 160 abuts the user's hands rather than the sharp needle tip penetrating his skin. The recessed needle 162 may be repeatedly used without risk of contamination.

The recessed needle 162 is the preferred needle for all uses not requiring that the needle enter into a patient's body. The recessed needle assembly may be used alone or in combination in a tandem relationship with a single-use needle. Use of the recessed needle for all purposes not requiring penetration of the patient's skin significantly reduces the overall risk of an accidental needle stick.

A single-use, over-cover device 200 to provide added protection is illustrated in FIGS. 21-26. The single-use, over-cover device provides further protection against an accidental needle stick by a contaminated needle by ensuring that the over-cover 200 of a contaminated needle may not be removed a second time. FIGS. 21-23 illustrate one embodiment of this one-time-use, protective needle cover 200. According to this invention, the hub of the needle 38, having vertical ridges 202, has a protective flange 204 between three of the four vertical ridges. Standard hubs, as used in the industry today, contain the vertical ridges 202 to permit gripping the hub for rotating the needle and also to prevent rotation of the cover 200 around the hub.

The protective over-cover 200 contains a lug member 206 on an interior surface thereof extending around approximately one-fourth of the internal circumference of the interior surface. The remainder of the interior surface of the cover 200 is smooth, as shown in the bottom portion of FIG. 23, such that it may slide over the extending flange 204. When the cover is placed over the needle during manufacture, the lug 206 is placed over that quadrant of the circumference of the hub which does not have flange 204 extending therefrom, as shown in FIGS. 21 and 22. The over-cover 200 may then be removed to permit use of the needle for a desired purpose. Preferably, the needle is a single-time-use needle, as illustrated in FIGS. 1-3, though other needles may be used. After the needle has been removed from the patient's body and is therefore contaminated, the protective collar 30 is slid up the needle to cover the sharp tip 56 of the needle 34 with blocking member 32 to ensure that accidental needle sticks will not occur, as described with respect to FIGS. 1-3. To further guard against accidental contamination, such as to open sores, the protective over-cover 200 is then placed over the entire needle assembly and hub to cover the entire length of the needle. The user placing the over-cover 200 onto the hub places the cover in a rotated relationship with respect to that from which it was removed from the hub, such that the lug portion 206 is in one of the four quadrants of the hub 38 having a flange 204. The lug 206 will make a distinct "click" as it engages the flange 204 and locks the protective over-cover 200 in position over the hub. The ridges 202 of hub 38 prevent the cover 200 from being rotated and thus from being removed from the hub. There are now two layers of puncture-proof material between the contaminated needle and the environment. If the tip of the needle assembly is accidentally bumped, the force is transferred from the over-cover 200 to the hub 38. The needle is completely shielded from being acted on by an external force. The entire needle assembly ma be safely removed from the syringe and disposed of in a conventional trash can due to the double-safety device now in place. If the tandem recessed needle as illustrated in FIG. 15 is in place, it may now be used or the syringe may be discarded with the needle in place.

Figure 24:
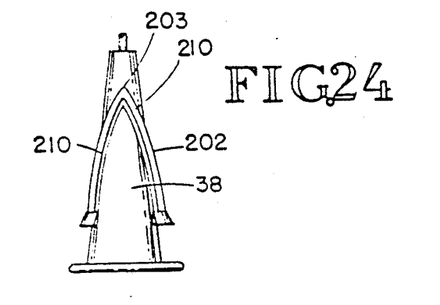
FIG. 24 is an alternative embodiment of the hub of the over-cap safety system.

An alternative over-cover locking mechanism is illustrated in FIG. 24. The hub 38 may include an inclined ridge 210 in addition to the ridges 202 normally present on the needle. The inclined ridge 210 serves as a safety device to prevent the user from accidentally placing the lug 206 into that quadrant of the hub which does not contain the flange 204. In the event the user is placing the cover 200 onto the hub in the wrong position, the inclined ridge 210 will cause the lug 206 to rotate away from the quadrant which does not contain the flange 204 and into a quadrant which does contain the flange 204. The inclined ridge 210 may be made with an interior slope surface which permits the cover 200 to be easily removed from the quadrant not having the flange 204 but prevents the flange from being returned to the quadrant not having the flange 204.

Figure 25:
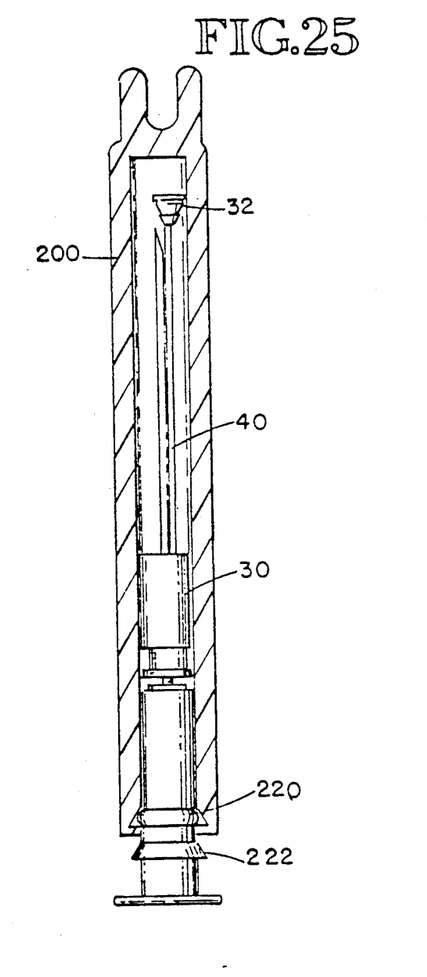
FIG. 25 is an alternative embodiment of the protective over-cap safety system using a two-stop hub member.
Figure 26:
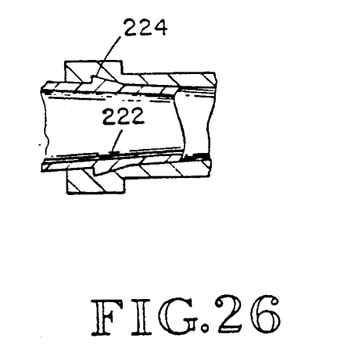
FIG. 26 is a cross-sectional view of the protective over-cap of FIG. 25, with the cap permanently locked in position.

An alternative over-cover removal and locking mechanism is illustrated in FIG. 25. The cover 200 is coupled to a hub having a first annular, relatively smooth protrusion 220 around the hub and an annular flange 222 located just below the annular protrusion. When the overcover 200 is placed on the hub 38 by the manufacturer, the interior surface of the over-cover device 200 engages the protrusion 202 and is resiliently held in position. The hub assembly as currently used in the industry is suitable for the upper portion of this hub or an additional protrusion 220 may be added if desired. The over-cover 200 is removable by a user to expose the needle and permit the needle to be used for its intended purpose. After the needle is used, the needle is safely covered using sleeve 30 and blocking member 32, as has been described herein with respect to FIGS. 1-3. The protective over-cover 200 is placed over the hub 38 to completely cover the needle assembly; however, the user presses over-cover 200 slightly further down from its initial position so that it engages the annular flange 222 in a locking relationship. The annular flange 222 mates with an interior annular region 224, as shown in FIG. 26, and permanently locks the overcover 200 onto the needle assembly. The needle assembly may now be removed from the syringe and disposed of as has been described herein.

The over-cover is preferably clear, or at least partially see-through, to permit a user to determine if the needle has been used or not and also to confirm the presence of the sleeve 30, blocking member 32, cord 40, etc.

This invention has been described with respect to numerous embodiments. Those skilled in the art will recognize that this invention may also be embodied in other devices which provide a similar function to obtain the same result as those devices described herein.

We claim:

1. A needle safety device comprising:
   a hub for coupling to a syringe;
   a needle coupled at a base thereof to said hub and having a sharp tip spaced away from said hub;
   a sleeve slidably coupled to said needle;
   a cord coupled to said hub and extending through said sleeve; and
   a blocking member coupled to said cord and having a flange for engaging an interior surface of said sleeve for retaining said blocking member in said sleeve, said cord having a length approximately equal to the length of said needle such that said blocking member is held adjacent the tip of said needle when said blocking member is in said sleeve.

2. The needle safety device of claim 1 wherein said interior surface of said sleeve prevents said blocking member from belong removed from said sleeve once said blocking member has been placed therein.

3. The needle safety device of claim 1 wherein said interior surface of said sleeve permits said blocking member to be removed from said sleeve after it has been placed therein 4. The needle safety device of claim 1 wherein an audible sound is emitted when said blocking member is engaged in said sleeve.

5. The needle safety device of claim 1 wherein said blocking member is spaced apart from said needle tip when said sleeve is near said base of said needle and is adjacent said needle tip when said sleeve is adjacent said needle tip.

6. The needle safety device of claim 1, further including a flexible-membrane coupled between said sleeve and said hub and extending around said needle.

7. The needle safety device of claim 1 wherein said blocking member is sufficiently soft that said needle tip may be embedded therein but is sufficiently dense that said needle tip may not extend through said blocking member.

8. An apparatus for preventing accidental needle sticks, comprising:
   a base member adapted to support a needle;
   a needle having a sharp tip and a base, the base of said needle being coupled to said base member;
   a cord coupled to said base member, the length of said cord being approximately equal to the distance form its coupling point on said base member to the tip of said needle;
   a puncture-proof blocking member coupled to said cord;
   a sleeve having a hollow shaft means therein, said cord and said needle extending through said hollow shaft means such that said sleeve is slidably coupled to said needle and to said cord; and
   a recess in a distal region of said sleeve, said recess being adapted to receive said blocking member for retaining said blocking member directly adjacent said sharp tip when said sleeve is adjacent said tip to prevent said sharp tip from entering an object when said sleeve is adjacent said tip.

9. The apparatus according to claim 8 wherein said cord is slightly longer than the distance from its coupling point on said base member to the tip of said needle to ensure that siad blocking member is pulled into said recess prior to said sleeve separating from said needle and is held slightly spaced from said tip.

10. The apparatus according to claim 8, further including a permanent locking member within said recess for preventing said blocking member from being removed from said recess after it has entered said recess.

11. The apparatus according to claim 8 wherein said recess includes a releasable locking member for releasable retaining said blocking member within said sleeve.

12. The apparatus according to claim 8 wherein said blocking member includes a lug region and said sleeve member includes a flange within said recess for mating with said lug region to retain said blocking member within said sleeve.

13. The apparatus according to claim 8 wherein said blocking member includes a top region extending above and overlying said sleeve such that if said apparatus strikes an object adjacent said tip, said blocking member strikes said object and enters said tip.

14. The apparatus according to claim 8 wherein said cord is a mono-filament fiber of a predetermined length and is inelastic in a direction along its length but is reflexible is a direction perpendicular to its length to permit said cord to bend back towards said base member, out of the way of a user when inserting the needle into an object.

15. The apparatus according to claim 14 wherein said cord is formed to be resiliently biased away from said tip and to hold said blocking member adjacent said base member when said sleeve is adjacent said base of said needle.

16. The apparatus according to claim 8 wherein said shaft means includes a single hollow shaft and said cord and said needle are both within said single shaft.

17. An apparatus according to claim 8 wherein said sleeve includes an external annular recess and further includes an over-cover having a forked member at a distal end thereof, said formed member being adapted to engage said annular recess for sliding said sleeve from a base region toward said tip.

* * * * *

UNITED STATES PATENT AND TRADEMARK OFFICE
CERTIFICATE OF CORRECTION

PATENT NO. : 5,013,305

DATED : May 7, 1991

INVENTOR(S) : Eric A. Opie; Fred E. Silverstein

It is certified that error appears in the above-identified patent and that said Letters Patent is hereby corrected as shown below:

In column 16, claim 2, line 17, please delete "belong" and substitute therefor -- being --.

In column 16, claim 3, line 22, after "therein" please insert -- . --.

In column 17, claim 14, line 19, please delete "reflexible" and substitute therefor -- flexible --.

Signed and Sealed this

First Day of December, 1992

Attest:

DOUGLAS B. COMER

*Attesting Officer*     *Acting Commissioner of Patents and Trademarks*